US012661465B2

(12) United States Patent
Alqarni et al.

(10) Patent No.: US 12,661,465 B2
(45) Date of Patent: Jun. 23, 2026

(54) METHOD FOR INTUBATING PATIENT WITH MAGNETIC BOUGIE SYSTEM

(71) Applicant: Imam Abdulrahman Bin Faisal University, Dammam (SA)

(72) Inventors: Abdulrahman Athwan S. Alqarni, Dammam (SA); Khalid Mohamad Morsy Ibraheem, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 584 days.

(21) Appl. No.: 18/310,870

(22) Filed: May 2, 2023

(65) Prior Publication Data

US 2024/0366891 A1     Nov. 7, 2024

(51) Int. Cl.
*A61M 16/04*          (2006.01)

(52) U.S. Cl.
CPC .... *A61M 16/0411* (2014.02); *A61M 16/0409* (2014.02); *A61M 16/0488* (2013.01)

(58) Field of Classification Search
CPC .... A61M 16/0411; A61M 16/04–0463; A61M 16/0475; A61M 16/0488; A61M 25/01–0108; A61M 25/0127; A61M 2025/0166; A61M 2025/09175; A61M 2205/3317
See application file for complete search history.

(56) References Cited

U.S. PATENT DOCUMENTS

| | | | |
|---|---|---|---|
| 4,063,561 A | 12/1977 | McKenna | |
| 4,244,362 A * | 1/1981 | Anderson ......... | A61M 16/0418 128/207.14 |
| 5,944,023 A | 8/1999 | Johnson et al. | |
| 6,672,308 B1 * | 1/2004 | Gaspari ............. | A61M 16/0488 128/207.14 |
| 10,653,307 B2 * | 5/2020 | Molnar .................. | A61B 1/018 |
| 11,426,549 B2 | 8/2022 | Brophy | |

(Continued)

FOREIGN PATENT DOCUMENTS

CN          207286429 U          5/2018

OTHER PUBLICATIONS

Bilge et al. ; Endotracheal Intubation by Paramedics Using Neodymium Magnet and Modified Stylet in Simulated Difficult Airway: A Prospective, Randomized, Crossover Manikin Study ; Hindawi, vol. 2019 ; Oct. 15, 2019 ; 13 Pages.

(Continued)

*Primary Examiner* — Brandy S Lee
*Assistant Examiner* — Sara K Toich
(74) *Attorney, Agent, or Firm* — Oblon, McClelland, Maier & Neustadt, L.L.P.

(57)          ABSTRACT

A method for intubating a patient with a magnetic bougie system is provided. The method includes inserting a bougie through an oral cavity of the patient and advancing the bougie to a trachea of the patient. The method further includes attracting a metal tip of the bougie to a magnet. The magnet is positioned externally to the trachea of the patient. The magnet is fixed to a base holder. The method further includes confirming a position of the bougie with one or more sensors. The method further includes inserting an endotracheal tube through the oral cavity of the patient and advancing the endotracheal tube to the position of the bougie.

18 Claims, 10 Drawing Sheets

(56)  References Cited

U.S. PATENT DOCUMENTS

| | | | |
|---|---|---|---|
| 2002/0066450 A1* | 6/2002 | Bonutti ................. | A61B 1/015 128/200.26 |
| 2010/0224186 A1* | 9/2010 | Uesugi .............. | A61M 16/0459 128/207.14 |
| 2010/0319702 A1* | 12/2010 | Wood ................ | A61M 16/0443 128/207.14 |
| 2014/0257080 A1 | 9/2014 | Dunbar et al. | |
| 2014/0275958 A1* | 9/2014 | Victor ................... | A61B 5/065 600/409 |
| 2017/0189634 A1* | 7/2017 | Larson .................. | A61B 1/267 |
| 2019/0388004 A1 | 12/2019 | Victor | |

OTHER PUBLICATIONS

Miyasaka et al. ; A Low-Cost, Point-of-Care Test for Confirmation of Nasogastric Tube Placement via Magnetic Field Tracking ; MDPI sensors ; Jun. 30, 2021 ; 17 Pages.

* cited by examiner

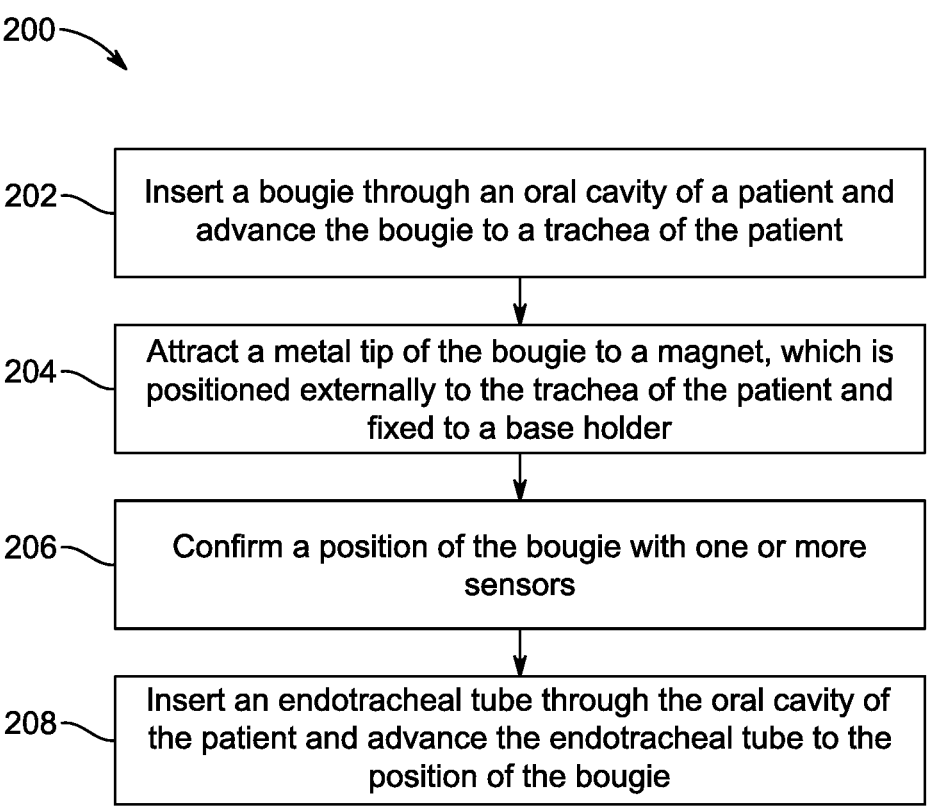

200

202 — Insert a bougie through an oral cavity of a patient and advance the bougie to a trachea of the patient 204 — Attract a metal tip of the bougie to a magnet, which is positioned externally to the trachea of the patient and fixed to a base holder 206 — Confirm a position of the bougie with one or more sensors 208 — Insert an endotracheal tube through the oral cavity of the patient and advance the endotracheal tube to the position of the bougie

FIG. 2

METHOD FOR INTUBATING PATIENT WITH MAGNETIC BOUGIE SYSTEM

BACKGROUND

Technical Field

The present disclosure is directed to a medical device used for endotracheal intubation procedure, and particularly, to a method for ensuring proper placement of an endotracheal tube in trachea of a patient.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

An endotracheal intubation procedure, otherwise known as an airway maintenance method, is performed for a patient who is suffering from respiratory failure, airway obstruction or a patient who needs breathing support while the patient is under anaesthesia. The endotracheal intubation procedure includes an endotracheal tube introducer, which is otherwise known as a bougie, for intubating an endotracheal tube into the trachea. During the intubation procedure, the bougie is intubated into the trachea through the mouth and then through the oral cavity. While using conventional methods of endotracheal intubation, several issues such as accidental insertion of the bougie into the esophagus, or insertion of the bougie to an incorrect distance, are faced. Furthermore, the time involved for x-ray confirmation for accurate positioning of the bougie may lead to several complications, especially in a patient suffering from pneuomothorax. Moreover, at some healthcare centres no such provisions are available.

U.S. Pat. No. 11,426,549 describes an apparatus for assisting proper placement of an endotracheal tube during patient intubation. An arcuate formed at a bottom surface of an external member is superposed on a patient's neck during intubation. The external member includes a proximity sensor and a magnet. An insertion member is movably coupled to an end member which includes a proximity tag member and a magnet member. The magnet member is configured to be attracted to the magnet to guide the endotracheal tube to the correct location. However, the external member is devoid of any means for efficient maneuvering or positioning of the external member over the patient's neck.

CN207286429 describes a conduit which includes a catheter body, a magnet, a power supply, a sensor, a data processor, and an alarm. A metalwork is embedded with a tip of the catheter body. The sensor is arranged between the magnet and an infant suprasternal notch. An input terminal of the data processor is connected with the sensor, and an output terminal is connected with the alarm. When attraction between the magnet and the metalwork reaches maximum, i.e., the distance between the magnet and the metalwork is minimum, the tip of the catheter body reaches desired position. Having several components for the intubation makes the procedure complex.

Accordingly, it is one object of the present disclosure to provide a simple method, apparatus and system which provide more control and manipulation during the endotracheal intubation procedure. It is also an object of the present disclosure to develop an efficient intubation system which can be fabricated with less complexity and having a tip of a bougie that can be controlled magnetically.

SUMMARY

In an exemplary embodiment, a method for intubating a patient with a magnetic bougie system is described. The method includes inserting a metal tip of a bougie through an oral cavity of the patient and advancing the metal tip of the bougie to a trachea of the patient. The method further includes positioning a base holder on an anterior surface of a neck of the patient. The method further includes attracting the metal tip of the bougie to a magnet. The magnet is positioned externally to the trachea of the patient. The magnet is fixed to a base holder. The method further includes positioning the metal tip of the bougie with the magnet. The method further includes confirming a position of the bougie with one or more sensors. The method further includes inserting an endotracheal tube through the oral cavity of the patient and advancing the endotracheal tube to the position of the metal tip of the bougie.

In some embodiments, positioning the metal tip of the bougie with the magnet includes at least one of changing the power of the magnet and changing the position of the base holder on the anterior surface of the neck of the patient. In some embodiments, positioning the metal tip of the bougie includes one or more of rotating, bending, flexing, straightening, moving, and manipulating the shape of the metal tip of the bougie in the neck of the patient.

In some embodiments, the method further includes inserting a laryngeal tube through the oral cavity of the patient and advancing the laryngeal tube to an esophagus of the patient before inserting the bougie. The method further includes inserting the metal tip of the bougie into a bougie port of the laryngeal tube. The method further includes removing the laryngeal tube from the esophagus of the patient while maintaining the position of the magnet and maintaining the position of the metal tip of the bougie in the trachea of the patient. The method further includes confirming the position of the metal tip of the bougie with at least one of a metal sensor and a magnet sensor.

In some embodiments, confirming the position of the metal tip of the bougie with at least one of the metal sensor and the magnet sensor includes confirming the position of the metal tip of the bougie at the trachea of the patient with a first sensor positioned at a thyroid cartilage of the patient, confirming the position of the metal tip of the bougie at a distal cuff of the laryngeal tube and along an axis of the laryngeal tube with a second sensor, and confirming the position of the metal tip of the bougie at the trachea of the patient with a third sensor positioned at a carina of the patient. The third sensor is the metal sensor that detects the metal tip of the bougie.

In some embodiments, the method further includes positioning the second sensor between the first sensor and the third sensor.

In some embodiments, the bougie port of the laryngeal tube has a diameter of from 0.7 to 0.9 times a diameter of the laryngeal tube.

In some embodiments, the position of the metal tip of the bougie is confirmed with at least one ultrasound imaging device.

In some embodiments, the method further includes confirming a location of the magnet with the ultrasound imaging device.

In some embodiments, the method further includes confirming a position of at least one of the first, second or third sensors on the throat of the patient with the ultrasound imaging device.

In some embodiments, the bougie port of the laryngeal tube is fabricated of polyvinyl chloride (PVC).

In some embodiments, at least two of the first, second and third sensors are metal sensors including a detector end fabricated of a same metal as the metal tip of the bougie.

In some embodiments, at least two of the first, second and third sensors are metal sensors including a detector end fabricated of a different metal than the metal tip of the bougie.

In some embodiments, the base holder is fabricated of PVC.

In some embodiments, the base holder includes at least two runners configured to position the base holder on the neck of the patient.

In some embodiments, the metal is at least one selected from the group consisting of stainless steel, copper, and aluminum.

In some embodiments, the metal tip is made of stainless steel and the metal sensors include the detector ends made of copper.

In some embodiments, the method further includes positioning the second sensor equidistant between the first sensor and the third sensor on the throat of the patient.

In some embodiments, the magnet is an electromagnet.

In some embodiments, the endotracheal tube has a metal segment.

In some embodiments, inserting the endotracheal tube through the oral cavity of the patient and advancing the endotracheal tube to the position of the metal tip of the bougie includes confirming the position of the metal segment of the endotracheal tube at the trachea of the patient with the third sensor positioned at the carina of the patient. In some embodiments, the third sensor detects the metal tip of the bougie and the metal segment of the endotracheal tube. In some embodiments, the detecting includes adjusting the position of the metal tip of the bougie and the metal segment of the endotracheal tube to maximize a detection signal. In some embodiments, a maximum signal is produced when the metal tip of the bougie and the metal segment of the endotracheal tube are positioned proximal to one another at the carina of the patient.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 2 is a schematic flow chart of a method for intubating the patient with the magnetic bougie system of FIG. 1, according to certain embodiments;

DETAILED DESCRIPTION

Figure 1:
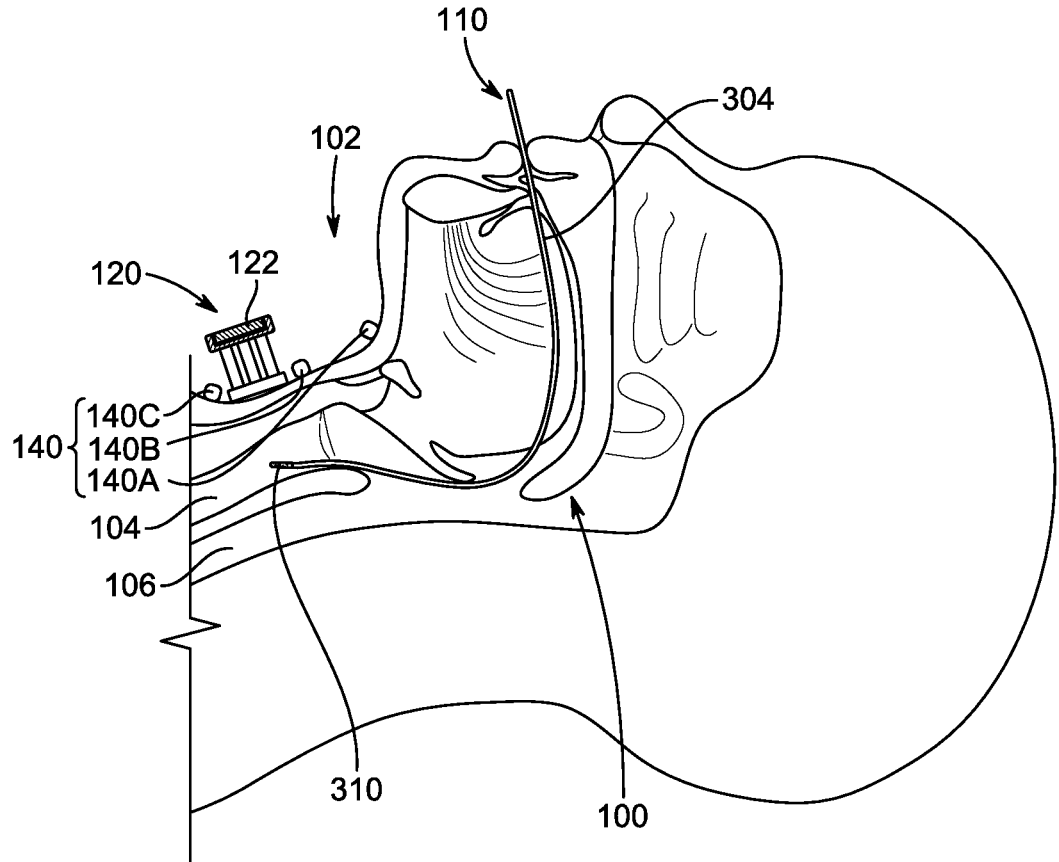
FIG. 1 is a schematic sectional view of a pharyngeal region of a patient that undergoes an endotracheal intubation procedure using a magnetic bougie system, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Aspects of the present disclosure are directed to a method for intubating a patient with a magnetic bougie system. The method includes placement of an endotracheal tube through an oral cavity of the patient and advancing the endotracheal tube to a position of an endotracheal tube introducer, otherwise referred to as 'the bougie'. As used herein, the term 'position' refers to a desired location of the metal tip of the bougie into a trachea of the patient using efficient magnetic forces and sensing methods during an endotracheal intubation procedure. As used herein, the term 'endotracheal intubation procedure' refers to a medical procedure in which the endotracheal tube is inserted into the trachea through the oral cavity of the patient. As used herein, the term 'endotracheal tube' refers to a tube generally fabricated of polyvinyl chloride (PVC) that is placed between vocal cords through the trachea. The method also includes usage of a laryngeal tube before the insertion of the bougie. The present disclosure uses magnetic forces to at least partially perform the endotracheal intubation procedure with a high rate of success.

Referring to FIG. 1, a schematic sectional view of a pharyngeal region 100 of a subject that undergoes an endotracheal intubation procedure using a magnetic bougie system 102 is illustrated, according to an embodiment of the present disclosure. As used herein, the term 'pharyngeal region 100' refers to a hollow passage inside the neck that starts behind a nose and ends at the top of a trachea 104 and an esophagus 106. In the present disclosure, the subject is a mammal, especially a human. In some embodiments, the subject may be an animal. Hereinafter, the term 'human' may be interchangeably referred to as 'the patient'. In the present disclosure, the endotracheal intubation procedure is performed utilizing the magnetic bougie system 102 including a bougie 110 and a base holder 120 having a magnet 122. The magnetic bougie system 102 is alternatively referred to as 'the system 102' (see FIG. 1). In some embodiments, the system 102 includes a laryngeal tube 130 (shown in FIG. 4) to perform the endotracheal intubation procedure. The system 102 further includes one or more sensors 140 configured to detect a position of the bougie 110 as the bougie 110 advances to the trachea 104 of the patient during the endotracheal intubation procedure. In the present disclosure, the system 102 includes the bougie 110 having an elongated body 304 and a metal tip 310. In the present disclosure, the system 102 includes a first sensor 140A positioned at a thyroid cartilage of the patient and configured to detect a position of the bougie 110 at the trachea 104 of the patient, a third sensor 140C positioned at a carina of the patient and configured to detect a position of the bougie 110 at the trachea 104 of the patient, and a second sensor 140B positioned between the first sensor 140A and the third sensor 140C.

Referring to FIG. 2, a schematic flow chart of a method 200 for intubating the patient with the magnetic bougie system 102 is illustrated, according to an embodiment of the present disclosure. The method 200 is described with reference to FIG. 3-FIG. 7C. The order in which the method 200 described is not intended to be construed as a limitation, and any number of the described method steps can be combined in any order to implement the method 200. Additionally, individual steps may be removed or skipped from the method 200 without departing from the spirit and scope of the present disclosure.

At step 202, the method 200 includes inserting the bougie 110 through the oral cavity of the patient and advancing the bougie 110 to the trachea 104 of the patient. The insertion of the bougie 110 may be done under direct visualization (using a laryngoscope) or indirect visualization (such as rigid fiberoptic laryngoscopy and rigid video laryngoscopy). As used herein, the term 'laryngoscope' refers to the device that is used to visualize the larynx and adjacent structures mainly for inserting the endotracheal tube into a tracheobronchial tree. Human manipulation is necessary during the insertion process.

Figure 3:
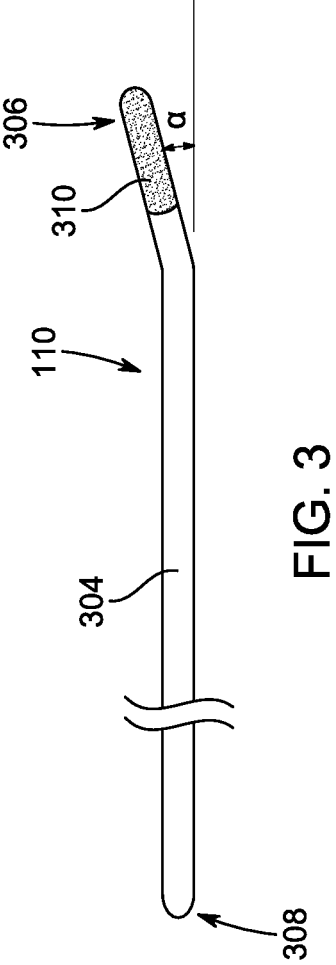
FIG. 3 is a schematic perspective view of a bougie of the magnetic bougie system of FIG. 1, according to certain embodiments.

As shown in FIG. 3, the bougie 110 includes the elongated body 304 having a tubular form and having a first end 306 and a second end 308. A practitioner inserts the first end 306 of the bougie 110 into the oral cavity of the patient by holding the second end 308 of the bougie 110. The second end 308 is substantially elliptical. The second end 308 of the elongated body 304 may also be spherical, or any other shape known in the art. The elongated body 304 may be equipped with devices such as an inflatable balloon to apply pressure against obstructions or narrowed walls, a gauge to measure pressure applied by the balloon, a wire, a hollow channel, and a light. The elongated body 304 may be fabricated from a material such as rubber, plastic, polytetrafluoroethylene, Teflon™, a non-thermoplastic material such as silicone, and a metal. In the present disclosure, the elongated body 304 is fabricated of polyvinyl chloride (PVC). The elongated body 304 may be coated in material such as fluoropolymers, silicones, parylenes, polyamides, and polyurethanes.

The elongated body 304 includes the metal tip 310 disposed at the first end 306 thereof. In the present disclosure, the metal tip 310 and the elongated body 304 may be an integral component. In some embodiments, the metal tip 310 may be detachably attached to the elongated body 304. In one embodiment, the metal tip 310 may be snap-fitted to the elongated body 304 at the first end 306 thereof. In some embodiments, the metal tip 310 may be flexibly attached to the elongated body 304. The metal tip 310 may be rigidly attached to the elongated body 304 to form a single body. The metal tip 310 may have a rounded tip shape to couple with the elongated body 304. In some embodiments, the shape of the metal tip 310 may be, but are not limited to, circular, rectangular, square, rhombic, or a polygon. The metal tip 310 is configured to bend at an angle 'α' relative to the elongated body 304. The angle 'α' defined between a longitudinal axis of the elongated body 304 and a longitudinal axis of the metal tip 310 is alternatively referred to as the metal tip angle 'α'.

In an embodiment, the metal tip angle 'α' may have a set value. In some embodiments, the metal tip angle 'α' may have a continuous range of values for easy maneuvering of the metal tip 310 during the endotracheal intubation procedure. The metal tip angle 'α' may have a value between 0 and 90 degrees. In an embodiment, the metal tip angle 'α' may be varied manually using an adjustment mechanism attached to the elongated body 304 or due to an inherent elastic property of the material of the elongated body 304. Particularly, the elongated body 304 may be made up of biodegradable and biocompatible PVC material such that the metal tip 310 can regain original position thereof after manipulation. The metal tip 310 is fabricated of a metal selected from the group consisting of stainless steel, copper, and aluminum. In the present disclosure, the metal tip 310 is made of stainless steel. The metal may include, but is not limited to, iron, tin, and titanium. In some embodiments, the metal tip 310 may be made up of a magnetic material such as cobalt, neodymium, gadolinium, dysprosium, holmium, and nickel. In some embodiments, the metal tip 310 may be fabricated with a non-magnetic material such as silver, and stainless steel. Further, the metal tip 310 may be made lighter than the elongated body 304 for easy maneuvering during the endotracheal intubation procedure.

The method 200 includes positioning the base holder 120 on an anterior surface of a neck of the patient. The patient may be lying in a posterior position in a face-up and front-facing position. The positioning of the base holder 120 may be done under direct visualization. Human manipulation may be necessary during the positioning process.

Figure 4:
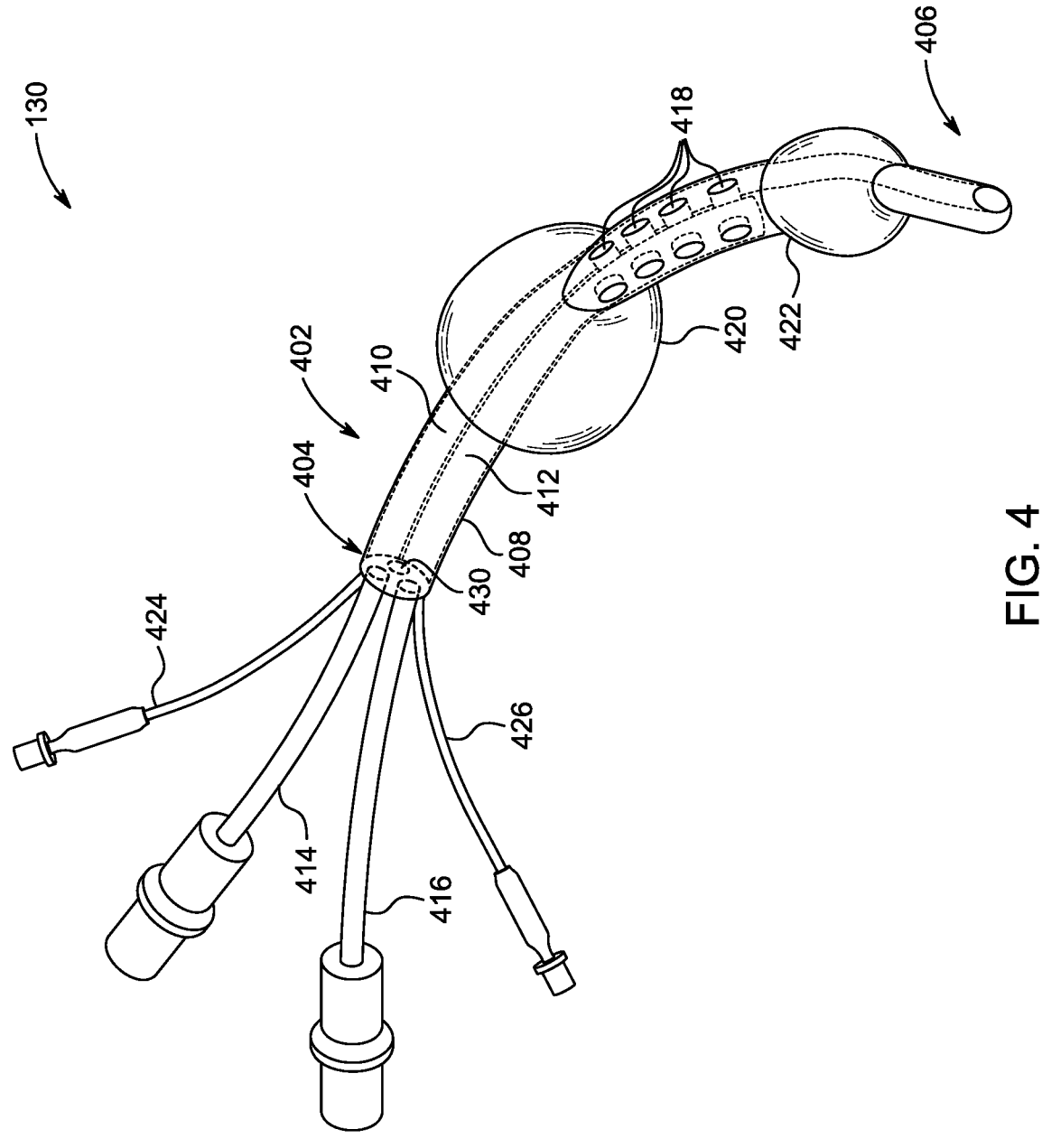
FIG. 4 is a schematic perspective view of a laryngeal tube, according to certain embodiments.

In some embodiments, the method 200 includes inserting the laryngeal tube 130 before the insertion of the bougie 110 and advancing the laryngeal tube 130 to the esophagus 106 of the patient. As shown in FIG. 4, the laryngeal tube 130 includes an elongated body 402 having a proximal end 404 configured to be placed outside the oral cavity of the patient and a distal end 406 configured to be placed in the esophagus 106 of the patient. The distal end 406 extends from the proximal end 404 of the elongated body 402 at an angle to facilitate easy insertion of the laryngeal tube 130 during the endotracheal intubation procedure. The elongated body 402 includes an outer wall 408 defining a circular cross-section. The elongated body 402 of the laryngeal tube 130 may be made of thermoplastic material such as PVC or non-thermoplastic material such as silicone. The elongated body 402 may be coated in material such as fluoropolymers, silicones, parylenes, polyamides, and polyurethanes.

The laryngeal tube 130 further includes a suction lumen 410 and a pharyngeal lumen 412 extending along a length of the elongated body 402. The suction lumen 410 is fluidly communicated with a suction conduit 414. The suction lumen 410 may include an open end at the proximal end 404 of the laryngeal tube 130 and an open end at the distal end 406 of the elongated body 402. The suction lumen 410 is configured to reduce a risk of aspiration in the trachea 104 of the patient. The pharyngeal lumen 412 defined in the elongated body 402 of the laryngeal tube 130 is fluidly communicated with a pharyngeal conduit 416. The pharyngeal lumen 412 may also include an open end at the proximal end 404 of the laryngeal tube 130 and communicated with a plurality of pharyngeal perforations 418 near the distal end 406. Particularly, the pharyngeal perforations 418 help to provide high ventilation capacities with less resistance within the laryngeal tube 130. The pharyngeal lumen 412 is configured to provide ventilation capacities such that the suction lumen 410 and the pharyngeal lumen 412 are together configured to facilitate easy airway management in the patient during a medical procedure.

The laryngeal tube 130 further includes a proximal cuff 420 disposed in a midway of the elongated body 402 and configured to secure a hypopharyngeal area of the patient. The laryngeal tube 130 further includes a distal cuff 422 disposed near the distal end 406 of the elongated body 402 and configured to prevent oxygen escape into a stomach of the patient. The proximal cuff 420 and the distal cuff 422 are inflated or deflated by a first cuff inflation line 424 and a second cuff inflation line 426, respectively, during the endotracheal intubation procedure. During the endotracheal intubation procedure, the proximal cuff 420 and the distal cuff 422 may be in a deflated condition. Upon inserting the laryngeal tube 130 through the oral cavity of the patient, the proximal cuff 420 may be inflated to firmly position the laryngeal tube 130 by engaging the inflated proximal cuff 420 with the hypopharyngeal area of the patient and the distal cuff 422 may be inflated to firmly position the distal end 406 of the laryngeal tube 130 in the esophagus 106 of the patient. The position of the laryngeal tube 130 can be confirmed by observing vapors in the laryngeal tube 130, chest rise, osculation, and by detecting exhaled carbon-dioxide.

Once the proximal cuff 420 and the distal cuff 422 of the laryngeal tube 130 are firmly positioned in the hypopharyngeal area and the esophagus 106 of the patient, the bougie 110 is inserted into the laryngeal tube 130. In the present disclosure, the method 200 includes inserting the bougie 110 into a bougie port 430 of the laryngeal tube 130. The bougie port 430 may be defined at the proximal end 404 of the laryngeal tube 130. The bougie port 430 may be further communicated with an opening (not shown) defined between the proximal cuff 420 and the distal cuff 422 via a passage extending along a length of the outer wall 408 of the laryngeal tube 130. As such, the bougie 110 may be inserted into the bougie port 430 and pass through the passage to exit through the opening. The bougie port 430 has a cylindrical cross section defining a diameter. In an embodiment, the bougie port 430 of the laryngeal tube 130 has the diameter of from 0.7 to 0.9, more preferably 0.75 to 0.85, and more preferably 0.77 to 0.82, times a diameter of the laryngeal tube 130. The bougie port 430 of the laryngeal tube 130 is also fabricated of PVC. In some embodiments, the bougie 110 may be inserted into the laryngeal tube 130 through the pharyngeal lumen 412 via the pharyngeal conduit 416 and released out into the trachea 104 via one of the pharyngeal perforations 418. In some embodiments, the pharyngeal perforations 418 may be replaced by a slit, in such a case, the bougie 110 may be released out into the trachea 104 via the slit of the elongated body 402. In some embodiments, the slit may be defined on an outer surface of the outer wall 408 of the laryngeal tube 130 along a length thereof. In such a case, the bougie 110 may be inserted through the slit and released out into the trachea 104 from an exit location defined between the proximal cuff 420 and the distal cuff 422.

Figure 5:
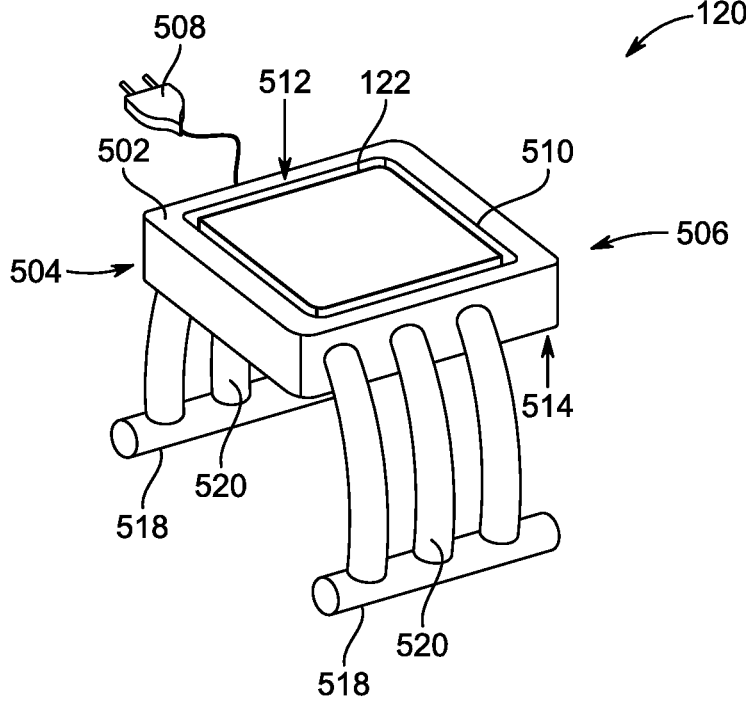
FIG. 5 is a schematic perspective view of a base holder of the magnetic bougie system of FIG. 1, according to certain embodiments.

At step 204, the method 200 includes attracting the metal tip 310 of the bougie 110 to the magnet 122. In the present disclosure, the magnet 122 is an electromagnet. In an example, attracting the metal tip 310 of the bougie 110 to the magnet 122 may include a magnetic flux of a certain strength. The magnetic flux may be varied depending on a surface area of the magnet 122 and a distance between the metal tip 310 of the bougie 110 and the magnet 122. As shown in FIG. 5, the magnet 122 is fixed to the base holder 120. The base holder 120 includes an elongated body 502 having a first end 504 and a second end 506. In one example, the elongated body 502 is in the form of a cuboid shape. In another example, the elongated body 502 may have a cubic shape, rectangular shape, or another shape known in the art. The base holder 120 further includes an electricity port 508 disposed between the first end 504 and the second end 506 thereof. The electricity port 508 is configured to couple with an electric source. In one embodiment, the electric source may be a battery. In another embodiment, the electric source may be a commercial power distribution line.

In case of the electromagnet, the electricity port 508 is communicated with a wire wound into a coil around a core to produce a magnetic field. The magnetic field of the magnet 122 may attract, engage, pull, draw close, and bring the metal tip 310 of the bougie 110 towards the magnet 122. The magnetic field of the magnet 122 is varied by varying electric currents of the power supply, and particularly, ampere rating of the current can be controlled to vary a strength of the magnetic field. Such capability of the magnet 122 allows the magnetic bougie system 102 to be used for patients of any age or skin size. The magnetic field of the magnet 122 may be an additive force, constructive force, or a force of attraction to attract the metal tip 310 of the bougie 110 to the magnet 122 during the endotracheal intubation procedure. In an example, during the endotracheal intubation procedure, depending on a distance between the magnet 122 and the metal tip 310 of the bougie 110, the power supply can be controlled to increase or decrease the magnetic field. It should be understood that the power supply to the electricity port 508 may be a conventional alternating current (AC) or direct current (DC) which is configured to provide the desired power to operate the magnet 122.

In some embodiments, the magnet 122 may be a permanent magnet. The magnet 122 may be made of a ferromagnetic material such as iron, nickel, and cobalt and their alloys, a paramagnetic material such as platinum and aluminum, and a diamagnetic material such as carbon and copper. It should be understood that the magnet 122 could be provided in alternate strengths and sizes in order to provide the desired objective discussed herein. The magnet 122 may have a rectangular shape to couple with the base holder 120. In some embodiments, the shape of the magnet 122 may be, but are not limited to, square, circular, rhombic, or a polygon. In the present disclosure, as shown in FIG. 5, the elongated body 502 of the base holder 120 may be provided with a depression 510 on a top surface 512 thereof to accommodate the magnet 122 therein. Further, the base holder 120 may include another magnet configured to hold the magnet 122 in the depression 510. In one embodiment, the magnet 122 may be fixed on the top surface 512 of the elongated body 502. In another embodiment, the magnet 122 may fixed on a bottom surface 514 of the elongated body 502. The magnet 122 may be centrally positioned in or on the base holder 120. In some embodiments, the magnet 122 may be positioned on a left or a right side of the top surface 512 or the bottom surface 514 of the base holder 120. In another embodiment, the magnet 122 may be positioned towards the first end 504 or the second end 506 on the top surface 512 or the bottom surface 514 of the base holder 120. The magnet 122 is fixed to the base holder 120 to provide support to the magnet 122 during the endotracheal intubation procedure. During the endotracheal intubation procedure, the base holder 120 is positioned on the neck of the patient so that the magnet 122 is positioned externally to the trachea 104 and the bougie 110 is inserted through the oral cavity of the patient. In an embodiment, the base holder 120 may be positioned on the anterior of the neck of the patient. The method 200 further includes removing the laryngeal tube 130 from throat of the patient while maintaining the position of the magnet 122. The magnet 122 is turned on by establishing an electric communication between the electric source and the magnet 122. The magnet 122 attracts the metal tip 310 such that the metal tip 310 enters the trachea 104 of the patient. The base holder 120 is also fabricated of PVC. The base holder 120 includes at least two runners 518 configured to position the base holder 120 on the neck of the patient. In one embodiment, the runners 518 may move the base holder 120 upwards along the neck towards a chin of the patient. In another embodiment, the runners 518 may move the base holder 120 downwards along the neck towards a chest of the patient. In an embodiment, the runners 518 may hold the base holder 120 in position. The two runners 518 have a cylindrical cross section that defines a diameter and have a length. Each runner 518 of the base holder 120 is connected to the bottom surface 514 or the side of the elongated body 502 of the base holder 120 via one or more vertical attachment columns 520. The vertical attachment columns 520 have a cylindrical cross section defining a diameter and have a length. The vertical attachment columns 520 may be straight or curved. In one embodiment, the length of the runner 518 is equal to the length of the vertical attachment columns 520. In another embodiment, the length of the runner 518 is greater than the length of the vertical attachment column 520. In some embodiments, the length of the vertical attachment column 520 is greater than the length of the runner 518. In one embodiment, the length of the runner 518 is equal to the length of the elongated body 502 of the base holder 120. In some embodiments, the length of the runner 518 is greater than the length of the elongated body 502 of the base holder 120. In another embodiment, the length of the elongated body 502 of the base holder 120 may be greater than the length of the runner 518. In an embodiment, one or more runner 518 is positioned on a front-facing left-medial and right-medial plane of the neck of the patient external to the trachea 104. In one example, the runners 518 may be positioned external to the trachea 104 on a sternohyoid, a thyrohyoid, and a sternothyroid muscle in the neck of a patient. The runners 518 may be positioned external to the trachea 104 on a thyroid cartilage of a larynx and a thyroid gland of the patient.

The method 200 includes positioning the metal tip 310 of the bougie 110 with the magnet 122. The positioning of the metal tip 310 of the bougie 110 may be done under direct visualization or indirect visualization. Human manipulation may be necessary during the positioning process.

According to the present disclosure, the positioning of the metal tip 310 of the bougie 110 with the magnet 122 includes at least one of changing the power of the magnet 122 and changing the position of the base holder 120 on the anterior surface of the neck of the patient. In an embodiment, changing the power of the magnet 122 may include increasing and decreasing the power. In some embodiments, changing the power of the magnet 122 may include changing the magnetic field and the magnetic flux. In an embodiment, changing the position of the base holder 120 on the anterior surface of the neck may include moving the base holder 120 upwards along the anterior surface towards a chin of the patient or downwards along the anterior surface towards a chest of the patient. In some embodiments, changing the position of the base holder 120 on the anterior surface of the neck may include moving the base holder 120 laterally along the neck of the patient to a left and a right side. In some embodiments, changing the position of the base holder 120 on the anterior surface of the neck may include tilting the first end 504 or the second end 506 the base holder 120 away from the neck of the patient.

According to the present disclosure, the positioning of the metal tip 310 of the bougie 110 with the magnet 122 further includes changing the position of the metal tip 310 of bougie 110, wherein changing the position of the metal tip 310 of the bougie 110 includes one or more of rotating, bending, flexing, straightening, moving, and manipulating the shape of the metal tip 310 of the bougie 110 in the neck of the patient. In an embodiment, rotating may be clockwise and counterclockwise. In some embodiments, bending may refer to bending, from a straight or previously bent position, the metal tip 310 of the bougie 110 at the angle 'α' relative to the elongated body 304. In some embodiments, flexing may refer to positioning the metal tip 310 of the bougie 110 in a bent position without changing the angle 'α' relative to the elongated body 304. In some embodiments, straightening may refer to straightening, from a previously bent position, the metal tip 310 of the bougie 110 so that the angle 'α' relative to the elongated body 304 is 0°. In another embodiment, moving may refer to moving the metal tip 310 of the bougie 110 from a first spot in the trachea 104 to at least a second spot in the trachea 104 of the patient. In this case, the first spot in the trachea 104 may be in a center of the trachea and the second spot in the trachea 104 of the patient may be against an inner wall of the trachea 104. In some cases, moving the metal tip 310 of the bougie 110 may include a third spot or more in the trachea 104 of the patient. In some embodiments, manipulating the shape may refer to making the metal tip 310 of the bougie 110 longer and shorter.

At step 206, the method 200 includes confirming a position of the bougie 110 with the one or more sensors 140. In some embodiments, the method 200 includes confirming the position of the bougie 110 with at least one of a metal sensor and a magnet sensor. As used herein, the terms 'metal sensor' and 'magnet sensor' refers to the sensors 140 which detect a position of the metal tip 310 of the bougie 110 made of the non-magnetic material and the magnetic material, respectively.

Figure 6A:
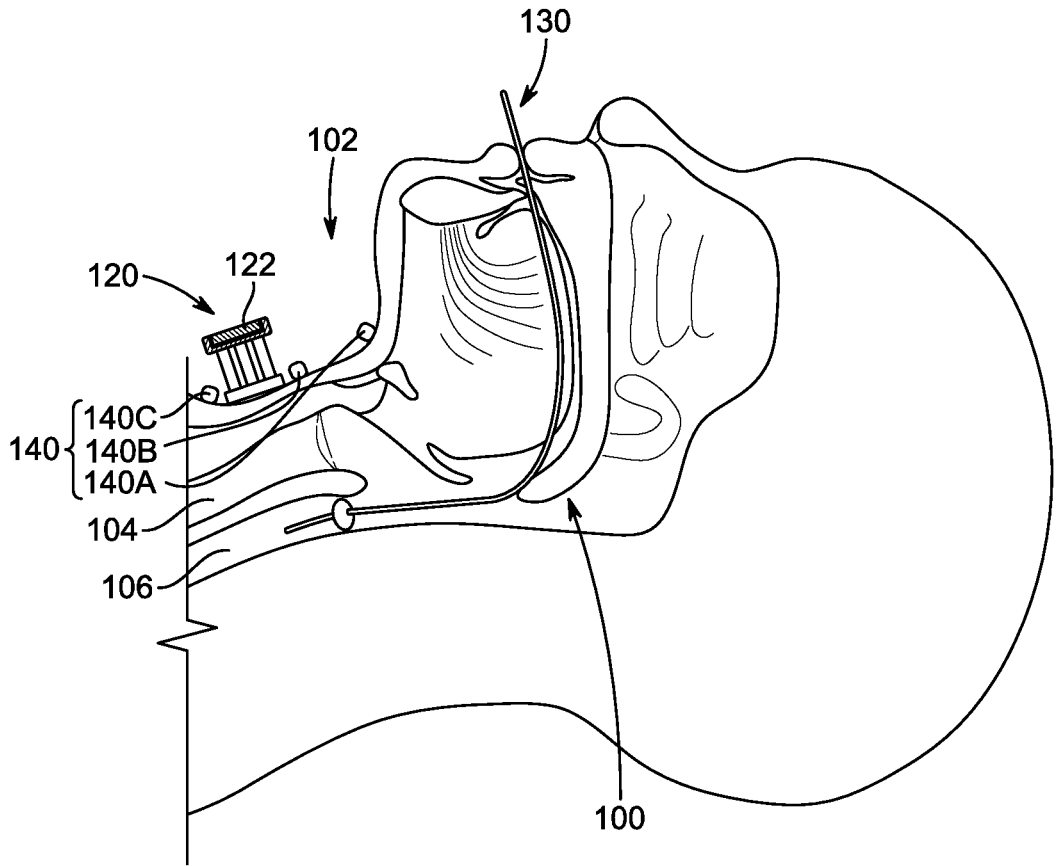
FIG. 6A is a schematic sectional view of the pharyngeal region showing placement of the base holder and sensors over neck of the patient, according to certain embodiments.

In the present disclosure, the one or more sensors 140 may be standalone devices which may be superposed on the neck of the patient, as shown in FIG. 6A. In such a case, the one or more sensors 140 may be positioned at different locations of the neck of the patient. The distal cuff 422 of the laryngeal tube 130 is shown inserted in the esophagus 106 of the patient in FIG. 6A. In some embodiments, the one or more sensors 140 may be detachably coupled to the bottom surface 514 of the base holder 120. In the case of multiple sensors 140, the sensors 140 may be positioned at different locations of the base holder 120 to confirm the position of the bougie 110 as the bougie 110 advances through the oral cavity during the endotracheal intubation procedure. In some embodiments, the one or more sensors 140 may be an integral component of the base holder 120.

According to the present disclosure, the magnetic bougie system 102 includes the first sensor 140A positioned at the thyroid cartilage of the patient and the third sensor 140C positioned at the carina of the patient. The method 200 further includes positioning the second sensor 140B between the first sensor 140A and the third sensor 140C. The first sensor 140A, the second sensor 140B, and the third sensor 140C are collectively referred to as 'the sensors 140' and individually referred to as 'the sensor 140' unless otherwise specifically mentioned. In some embodiments, the method 200 includes positioning the second sensor 140B equidistant between the first sensor 140A and the third sensor 140C on the throat of the patient. In some embodiments, at least two of the first sensor 140A, the second sensor 140B and the third sensor 140C are metal sensors including a detector end configured to detect a position of the metal tip 310 of the bougie 110. Particularly, the third sensor 140C is the metal sensor and configured to detect the position of the metal tip 310 of the bougie 110. One of the first, second, and third sensors 140A, 140B, and 140C is a magnet sensor. In some embodiments, at least two of the first sensor 140A, the second sensor 140B, and the third sensor 140C are the metal sensors including the detector end fabricated of the same metal as the metal tip 310 of the bougie 110. In some embodiments, at least two of the first sensor 140A, the second sensor 140B, and the third sensor 140C are the metal sensors including the detector end fabricated of a different metal than the metal tip 310 of the bougie 110. In the present disclosure, the metal sensors include the detector ends made of copper. In some embodiments, the metal sensors may include metals such as, but are not limited to, aluminum, iron, stainless-steel, and tin. In some embodiments, the detector end may be movably coupled to the base holder 120 such that a distance between the detector end and the skin surface of the patient may be adjusted based on age and skin size of the patient for desired sensing capability. In one example, the one or more sensors 140 may be radio frequency sensors. In another example, the one or more sensors 140 may be proximity sensors. As used herein, the term 'proximity sensing' refers to the ability of a sensor to detect the presence of nearby objects without any physical contact.

Figure 6B:
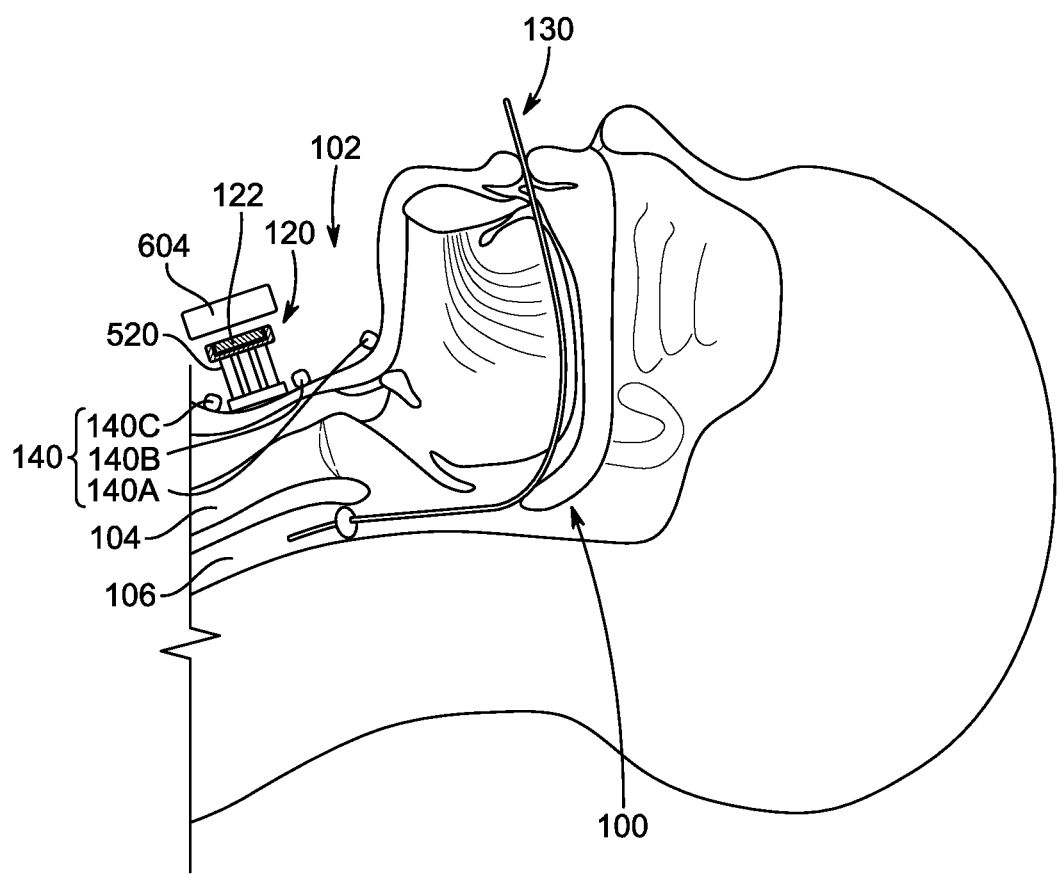
FIG. 6B is a schematic sectional view of the pharyngeal region showing placement of the base holder, the sensors and an ultrasound imaging device over the neck of the patient, according to certain embodiments.

In some embodiments, as shown in FIG. 6B, the position of the bougie 110 may be confirmed with at least one ultrasound imaging device 604 which may scan the position of the metal tip 310 and display the same on an interface of a smart device (such as a monitor, a smart phone, a smart watch, smart glasses, tablets, and phablets) of the practitioner. In an embodiment, the base holder 120 may be configured to hold an ultrasound scanning probe of the ultrasound imaging device 604. In some embodiments, the method 200 further includes confirming a location of the magnet 122 with the ultrasound imaging device 604. In some embodiments, the method 200 further includes confirming a position of at least one of the first sensor 140A, the second sensor 140B, or the third sensor 140C on the throat of the patient with the ultrasound imaging device 604. The ultrasound imaging device 604 may help to display the position of the magnet 122 and the one or more sensors 140 with respect to the metal tip 310 of the bougie 110. In some embodiments, the ultrasound imaging device 604 may be a standalone device coupled to the base holder 120. In an embodiment, the one or more sensors 140 may be replaced by the ultrasound imaging device 604. In an alternate embodiment, the ultrasound imaging device 604 may be additionally present with the one or more sensors 140, as shown in FIG. 6B. The distal cuff 422 of the laryngeal tube 130 is shown inserted in the esophagus 106 of the patient in FIG. 6B.

In some embodiments, the one or more sensors 140 may be associated with a first audio indicator for the confirmation of the position of the metal tip 310 of the bougie 110 within the trachea 104. The first audio indicator may include an audio alarm such as a bell, a toll, a ring, a beep, or an audio alert. The alarm may produce a sound to notify the practitioner regarding the position of the metal tip 310 of the bougie 110. The first audio indicator may be a first audio alert to indicate the confirmation of the position of the metal tip 310 of the bougie 110 within the trachea 104 of the patient. The first audio indicator may be a second audio alert to indicate the failed confirmation of the position of the metal tip 310 of the bougie 110 within the trachea 104 of the patient. In some embodiments, the one or more sensors 140 may be associated with a first visual indicator for the confirmation of the position of the metal tip 310 of the bougie 110. The first visual indicator may include blinking of light emitting diodes (LEDs), change in color of the LEDs, turning on/off the LEDs to notify the practitioner. In one embodiment, the first visual indicator may be a green color LED signal to indicate the confirmation of the position of the metal tip 310 of the bougie 110 within the trachea 104 of the patient. In another embodiment, the first visual indicator may be a red color LED signal to indicate the failed confirmation of the position of the metal tip 310 of the bougie 110 within the trachea 104 of the patient. In some embodiments, the first audio and the first visual indicators may be coupled to the base holder 120. In some embodiments, the sensors 140 may detect the position of the metal tip 310 of the bougie 110 through the first audio indicator, the first visual indicator, or a combination thereof.

Figure 7A:
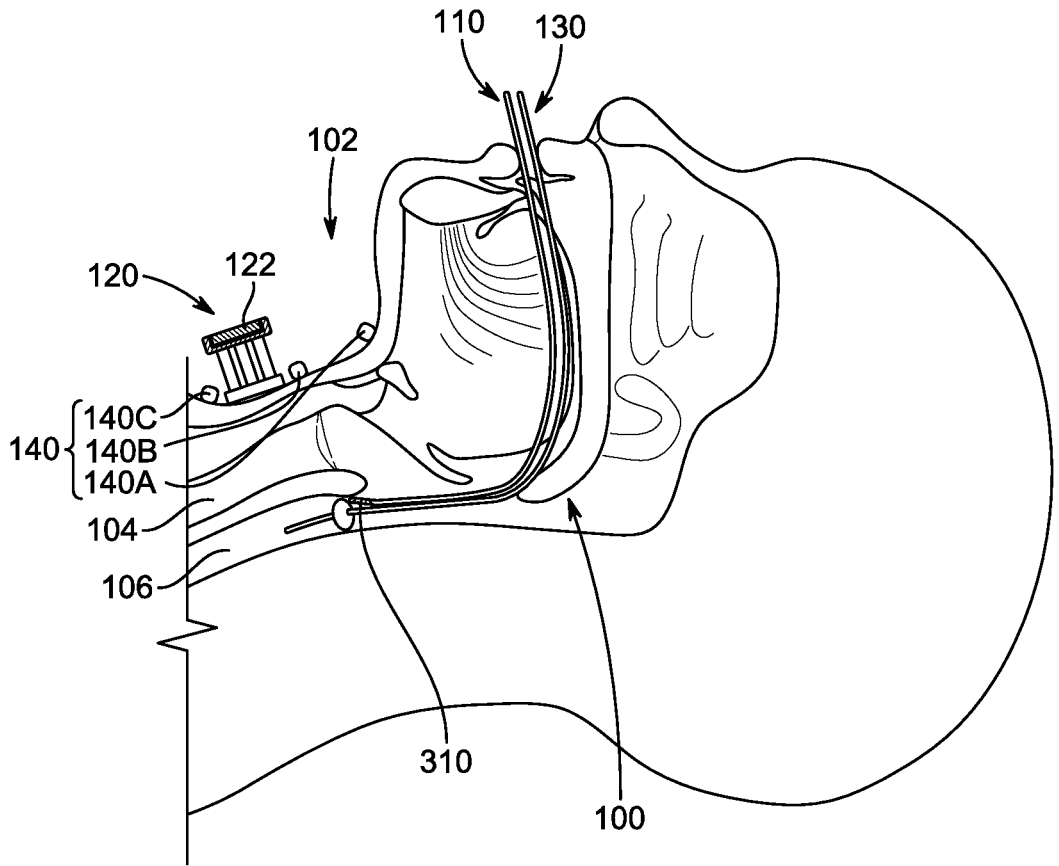
FIG. 7A is a schematic sectional view of the pharyngeal region of the patient showing insertion of the bougie along with the laryngeal tube, according to certain embodiments.
Figure 7B:
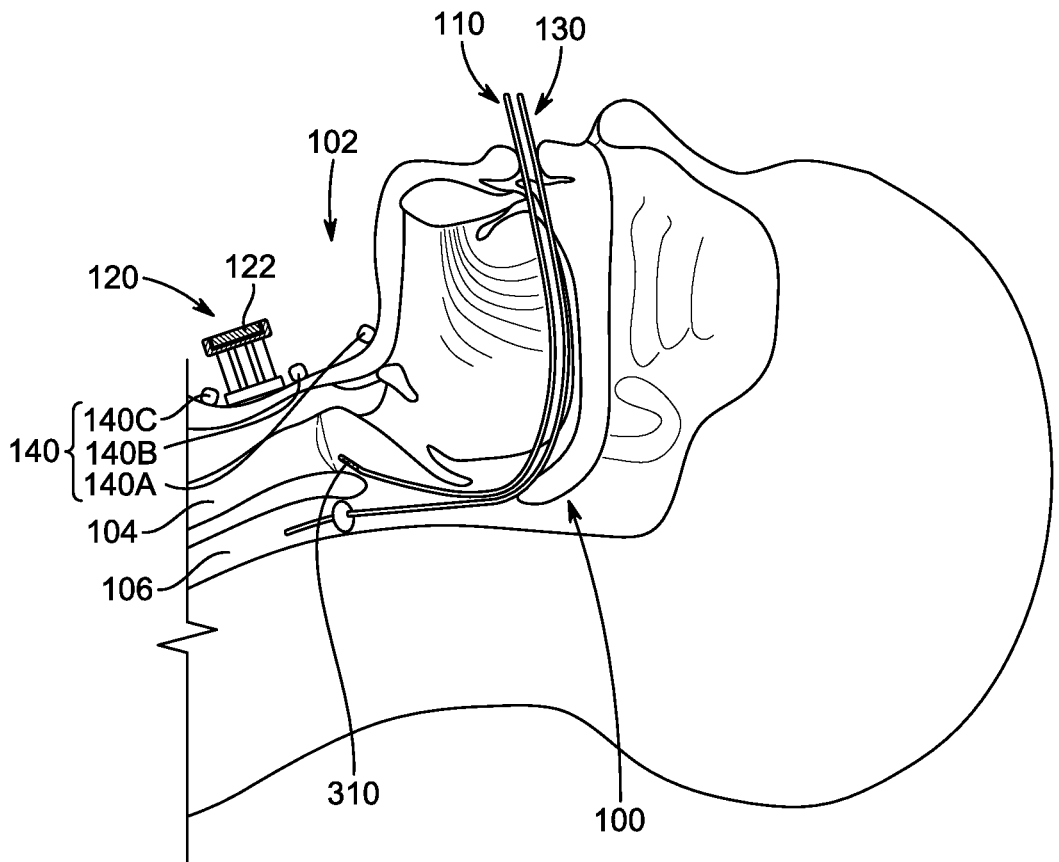
FIG. 7B is a schematic sectional view of the pharyngeal region of the patient showing attraction of the metal tip of the bougie by a magnet of the base holder, according to certain embodiments.
Figure 7C:
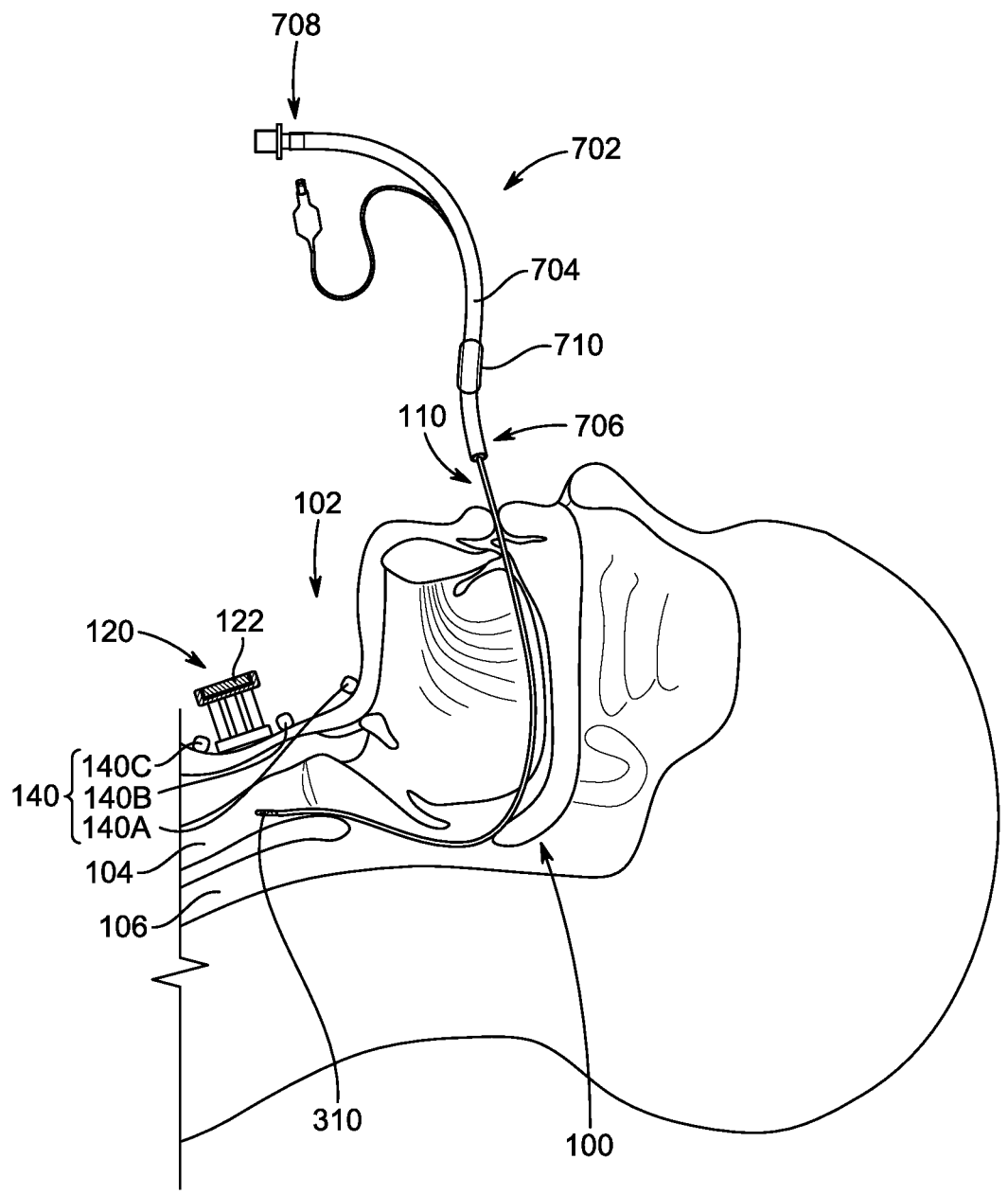
FIG. 7C is a schematic sectional view of the pharyngeal region of the patient showing placement of the bougie in the trachea of the patient and insertion of an endotracheal tube, according to certain embodiments.

According to the present disclosure, the first sensor 140A, the second sensor 140B, and the third sensor 140C may be able to detect the metal tip 310 of the bougie 110 if the metal tip 310 is positioned inside the trachea 104 of the patient. The sensors 140 may not detect the metal tip 310 of the bougie 110 if the metal tip 310 resides in the esophagus 106 of the patient, as shown in FIG. 7A. The position of the laryngeal tube 130 and the bougie 110 is schematically shown in FIG. 7A for the illustration purpose of the present disclosure. In some embodiments, the bougie 110 may be inserted into the laryngeal tube 130. The method 200 of confirming the position of the bougie 110 with the at least one of the metal sensor and the magnet sensor includes confirming the position of the bougie 110 at the trachea 104 of the patient with the first sensor 140A positioned at the thyroid cartilage of the patient. The first sensor 140A, particularly, helps to confirm the guidance for the bougie 110 through vocal cord into the trachea 104. The method 200 further includes confirming the position of the bougie 110 at the distal cuff 422 of the laryngeal tube 130 and along an axis of the laryngeal tube 130 with the second sensor 140B, as shown in FIG. 7B. In such position of the metal tip 310, the third sensor 140C fails to detect the position of the metal tip 310 of the bougie 110 as the metal tip 310 is present at the vocal cords of the patient. In an example that the third sensor 140C fails to detect the position of the metal tip 310 of the bougie 110, the third sensor 140C may indicate the audio alarm or the first visual indicator of a red color LED signal. As shown in FIG. 7C, the magnet 122 attracts the metal tip 310 of the bougie 110 and directs the metal tip 310 away from the esophagus 106 into the trachea 104 of the patient. As the bougie 110 is inserted further, the metal tip 310 of the bougie 110 passes through the trachea 104. The method 200 further includes confirming the position of the bougie 110 at the trachea 104 of the patient with the third sensor 140C positioned at the carina of the patient. Particularly, the third sensor 140C detects the metal tip 310 of the bougie 110 if the metal tip 310 is at the carina of the patient. Otherwise, the distal cuff 422 of the laryngeal tube 130 prevents the advancement of the metal tip 310 towards the third sensor 140C. Upon confirming the position of the bougie 110 in the trachea 104 of the patient, the method 200 includes removing the laryngeal tube 130 from the throat of the patient while maintaining the position of the magnet 122 and maintaining the position of the bougie 110 in the trachea 104 of the patient. The proximal cuff 420 and the distal cuff 422 are deflated to remove the laryngeal tube 130 from the throat of the patient.

At step 208, the method 200 includes inserting an endotracheal tube 702 through the oral cavity of the patient and advancing the endotracheal tube 702 to the position of the bougie 110. The endotracheal tube 702 includes an elongated body 704 having a distal end 706 configured to be placed in the trachea 104 of the patient and a proximal end 708. The endotracheal tube 702 further includes a cuff 710 at the distal end 706. Upon confirming the position of the bougie 110 in the trachea 104 of the patient, the distal end 706 of the endotracheal tube 702 is inserted next to or around the bougie 110 and placed in the trachea 104 of the patient. The cuff 710 is inflated to snugly fit the endotracheal tube 702 in the trachea 104 of the patient. The endotracheal tube 702 provides oxygen and inhaled gases to the lungs and protects the lungs from contamination, such as gastric contents or blood. Furthermore, the insertion of the endotracheal tube 702 inside the trachea 104 maintains an open airway or serves as a conduit through which to administer certain drugs and gases. Particularly, the endotracheal tube 702 also keeps the trachea 104 open in order to give oxygen, medicine, or anesthesia. The endotracheal tube 702 supports breathing in certain illnesses, such as pneumonia, emphysema, heart failure, collapsed lung or severe trauma. Furthermore, the endotracheal tube 702 removes blockages from the airway.

In the present disclosure, the endotracheal tube 702 has a metal segment. In some embodiments, the metal segment may be a flat piece of metal embedded within a wall of the elongated body 704 of the endotracheal tube 702. In other embodiments, the metal segment may be a raised piece of metal positioned on a front-facing exterior surface of the elongated body 704 of the endotracheal tube 702. In an embodiment, the metal segment may be, but is not limited to, the shape of a sphere and a cube on an interior of the endotracheal tube 702. In some embodiments, the metal segment may be, but is not limited to, the shape of a disc, a square, a rectangle, a circle, a rhombus, and a polygon. In some embodiments, the metal segment may be a metal tip at the distal end 706 of the endotracheal tube 702. The metal segment may be fabricated of a metal selected from the group consisting of stainless steel, copper, and aluminum. The metal may include, but is not limited to, iron, tin, and titanium. In some embodiments, the metal segment may be made up of a magnetic material such as cobalt, neodymium, gadolinium, dysprosium, holmium, and nickel. In some embodiments, the metal segment may be fabricated with a non-magnetic material such as silver, and stainless steel. Further, the metal segment may be made lighter than the elongated body 704 for easy maneuvering during the endotracheal intubation procedure. The metal segment of the endotracheal tube 702 may be attracted to the magnet 122 of the base holder 120 and the metal tip 310 of the bougie 110 for easy positioning of the endotracheal tube 702 during the endotracheal intubation procedure.

In the present disclosure, the metal segment of the endotracheal tube 702 may be inserted through the oral cavity of the patient and advanced to the metal tip 310 of the bougie 110 inside the trachea 104 of the patient. In some embodiments, the third sensor 140C positioned at the carina of the patient may confirm the position of the metal segment of the endotracheal tube 702 by detecting the metal tip 310 of the bougie and the metal segment of the endotracheal tube 702. In other embodiments, the third sensor 140C positioned at the carina of the patient may confirm the position of the metal segment of the endotracheal tube 702 by detecting the metal segment of the endotracheal tube 702 positioned proximal to the metal tip 310 of the bougie 110 inside the trachea 104 of the patient. In some embodiments, detecting and confirming the position of the metal tip 310 of the bougie 110 and the metal segment of the endotracheal tube 702 includes adjusting the position of the metal tip 310 of the bougie 110 and the metal segment of the endotracheal tube 702 to maximize a detection signal. In some embodiments, adjusting the metal tip 310 of the bougie 110 and the metal segment of the endotracheal tube 702 may include one or more of rotating, flexing, straightening, moving, and manipulating the shape of the metal tip 310 of the bougie 110 and the metal segment of the endotracheal tube 702 in the neck of the patient.

In some embodiments, adjusting of the metal tip 310 of the bougie 110 and the metal segment of the endotracheal tube 702 may include changing the position of the metal tip 310 of bougie 110 and the metal segment of the endotracheal tube 702, wherein adjusting the position of the metal tip 310 of the bougie 110 and the metal segment of the endotracheal tube 702 may include one or more of rotating, flexing, straightening, and moving the metal tip 310 of the bougie 110 and the metal segment of the endotracheal tube 702 in the neck of the patient. In an embodiment, rotating may be clockwise and counterclockwise. In some embodiments, flexing may refer to positioning the metal tip 310 of the bougie 110 and the metal segment of the endotracheal tube 702 in a bent position. In some embodiments, straightening may refer to straightening, from a previously bent position, the metal tip 310 of the bougie 110 and the metal segment of the endotracheal tube 702. In another embodiment, moving may refer to moving the metal tip 310 of the bougie 110 and the metal segment of the endotracheal tube 702 from a first spot in the trachea 104 to at least a second spot in the trachea 104 of the patient. In this case, the first spot in the trachea 104 may be in a center of the trachea and the second spot in the trachea 104 of the patient may be against an inner wall of the trachea 104. In some cases, moving the metal tip 310 of the bougie 110 and the metal segment of the endotracheal tube 702 may include a third spot or more in the trachea 104 of the patient. In some embodiments, adjusting the metal tip 310 of the bougie 110 and the metal segment of the endotracheal tube 702 produces a maximum signal when the metal segment of the endotracheal tube 702 if the metal segment of the endotracheal tube 702 is positioned proximal to the metal tip 310 of the bougie 110 inside the trachea 104 at the carina of the patient. The sensor 140C may not detect the metal segment of the endotracheal tube 702 resides in the esophagus 106 of the patient.

In some embodiments, the third sensor 140C may produce the maximum signal associated with the confirmation of the position of the metal segment of the endotracheal tube 702 at the metal tip 310 of the bougie 110 is distinguishable from the signals produced by the indicators associated with the confirmation of the position of the metal tip 310 of the bougie 110. In some embodiments, the maximum signal may be associated with a second audio indicator for the confirmation of the position of the metal segment of the endotracheal tube 702 at the metal tip 310 of the bougie 110. In some embodiments, the maximum signal may be associated with a second visual indicator for the confirmation of the position of the metal segment of the endotracheal tube 702 at the metal tip 310 of the bougie 110. In some embodiments, the second audio and the second visual indicators may be coupled to the base holder 120. In some embodiments, the third sensor 140C may confirm the position of the metal segment of the endotracheal tube 702 at the metal tip 310 of the bougie 110 through a maximum signal associated with the second audio indicator, the second visual indicator, or a combination thereof.

According to the present disclosure, the magnetic bougie system 102 and the method 200 of intubating the patient with the magnetic bougie system 102 helps the practitioner to correctly position the endotracheal tube 702 via the bougie 110. The magnetic bougie system 102 of the present disclosure is simple and compact. Furthermore, the components required to fabricate the magnetic bougie system 102 are easily available and cost effective. Moreover, the presence of the electromagnet in the magnetic bougie system 102 allows the practitioner to alter the magnetic power of the magnet 122 as per the requirements. The sensors 140 detect when the metal tip 310 is present inside the trachea 104 of the patient. Furthermore, the magnetic bougie system 102 allows easy maneuvering of the bougie 110 inside the pharyngeal region 100 till the metal tip 310 reaches the correct position in the trachea 104. The magnetic bougie system 102 is devoid of an external source for examining the position of the metal tip 310 inside the trachea 104 of the patient as the ultrasound imaging device 604 helps to achieve the desired work.

Numerous modifications and variations of the present disclosure are possible in light of the above teachings. It is therefore to be understood that within the scope of the appended claims, the invention may be practiced otherwise than as specifically described herein.

The invention claimed is:

1. A method for intubating a patient with a magnetic bougie system, comprising:
   inserting a laryngeal tube through the oral cavity of the patient and advancing the laryngeal tube to an esophagus of the patient;
   inserting the metal tip of the bougie into a bougie port of the laryngeal tube and advancing the metal tip of the bougie to a trachea of the patient;
   positioning a base holder on an anterior surface of a neck of the patient;
   attracting the metal tip of the bougie to a magnet, wherein the magnet is positioned externally to the trachea of the patient and wherein the magnet is fixed to the base holder;
   positioning the metal tip of the bougie with the magnet;
   removing the laryngeal tube from the esophagus of the patient while maintaining the position of the magnet and maintaining the position of the metal tip of the bougie in the trachea of the patient;
   and confirming the position of the metal tip of the bougie with at least one of a metal sensor and a magnet sensor, and inserting an endotracheal tube through the oral cavity of the patient and advancing the endotracheal tube to the position of the metal tip of the bougie;
   wherein confirming the position of the metal tip of the bougie with at least one of the metal sensor and the magnet sensor includes:

confirming the position of the metal tip of the bougie with a first sensor positioned at a thyroid cartilage of the patient;
   confirming the position of the metal tip of the bougie at a distal cuff of the laryngeal tube and along an axis of the laryngeal tube with a second sensor; and
   confirming the position of the metal tip of the bougie at the trachea of the patient with a third sensor positioned at a carina of the patient, wherein the third sensor is the metal sensor that detects the metal tip of the bougie.

2. The method of claim 1, wherein positioning the metal tip of the bougie with the magnet includes:
   at least one of changing the power of the magnet and changing the position of the base holder on the anterior surface of the neck of the patient; and
   wherein positioning the metal tip of the bougie includes one or more of rotating, bending, flexing, straightening, moving, and manipulating the shape of the metal tip of the bougie in the neck of the patient.

3. The method of claim 1, further comprising:
   positioning the second sensor between the first sensor and the third sensor.

4. The method of claim 1, wherein the bougie port of the laryngeal tube has a diameter of from 0.7 to 0.9 times a diameter of the laryngeal tube.

5. The method of claim 2, wherein the position of the metal tip of the bougie is further confirmed with at least one ultrasound device.

6. The method of claim 1, further comprising:
   confirming a location of the magnet with an ultrasound imaging device.

7. The method of claim 1, wherein the bougie port of the laryngeal tube is fabricated of polyvinyl chloride (PVC).

8. The method of claim 1, wherein at least two of the first, second and third sensors are metal sensors comprising a detector end fabricated of a same metal as the metal tip of the bougie.

9. The method of claim 1, wherein at least two of the first, second and third sensors are metal sensors comprising a detector end fabricated of a different metal than the metal tip of the bougie.

10. The method of claim 1, wherein the base holder is fabricated of PVC.

11. The method of claim 1, wherein the base holder comprises at least two runners configured to position the base holder on the neck of the patient.

12. The method of claim 7, wherein the metal tip of the bougie is at least one selected from the group consisting of stainless steel, copper, and aluminum.

13. The method of claim 8, wherein the metal tip of the bougie is made of stainless steel and the metal sensors comprise the detector ends made of copper.

14. The method of claim 1, further comprising:
   positioning the second sensor equidistant between the first sensor and the third sensor on the throat of the patient.

15. The method of claim 1, wherein the magnet is an electromagnet.

16. The method of claim 1, wherein the endotracheal tube has a metal segment.

17. The method of claim 16, wherein inserting the endotracheal tube through the oral cavity of the patient and advancing the endotracheal tube to the position of the metal tip of the bougie includes:
   confirming the position of the metal segment of the endotracheal tube at the trachea of the patient with the third sensor positioned at the carina of the patient, wherein the third sensor detects the metal tip of the bougie and the metal segment of the endotracheal tube, wherein the detecting includes adjusting the position of the metal tip of the bougie and the metal segment of the endotracheal tube to maximize a detection signal, and wherein a maximum signal is produced when the metal tip of the bougie and the metal segment of the endotracheal tube are positioned proximal to one another at the carina of the patient.

18. A method for intubating a patient with a magnetic bougie system, comprising:

inserting a metal tip of a bougie through an oral cavity of the patient and advancing the metal tip of the bougie to a trachea of the patient;

positioning a base holder on an anterior surface of a neck of the patient;

attracting the metal tip of the bougie to a magnet, wherein the magnet is positioned externally to the trachea of the patient and wherein the magnet is fixed to the base holder;

positioning the metal tip of the bougie with the magnet;

confirming a position of the metal tip of the bougie with a first sensor positioned at a thyroid cartilage of the patient, confirming the position of the metal tip of the bougie at a distal cuff of the laryngeal tube and along an axis of the laryngeal tube with a second sensor; and confirming the position of the metal tip of the bougie at the trachea of the patient with a third sensor positioned at a carina of the patient, wherein the third sensor is a metal sensor that detects the metal tip of the bougie; and inserting an endotracheal tube through the oral cavity of the patient and advancing the endotracheal tube to the position of the metal tip of the bougie;

confirming a position of at least one of the first, second or third sensors positioned on a throat of the patient with an ultrasound imaging device.

* * * * *